US007846173B2

(12) United States Patent
Sirh

(10) Patent No.: US 7,846,173 B2
(45) Date of Patent: Dec. 7, 2010

(54) PUNCTURING GUIDANCE TUBE FOR A LONG AND FINE NEEDLE

(76) Inventor: Heon Man Sirh, 106-1105 Sin Hyundai Apt., Apgujeong-Dong, Gangnam-Gu, Seoul 135-786 (KR) 135-786

( * ) Notice: Subject to any disclaimer, the term of this patent is extended or adjusted under 35 U.S.C. 154(b) by 173 days.

(21) Appl. No.: 11/989,632

(22) PCT Filed: May 4, 2006

(86) PCT No.: PCT/KR2006/001684

§ 371 (c)(1),
(2), (4) Date: Jan. 29, 2008

(87) PCT Pub. No.: WO2007/015595

PCT Pub. Date: Feb. 8, 2007

(65) Prior Publication Data

US 2009/0093834 A1 Apr. 9, 2009

(30) Foreign Application Priority Data

Aug. 1, 2005 (KR) ..................... 10-2005-0070226

(51) Int. Cl.
*A61B 17/34* (2006.01)

(52) U.S. Cl. ..................................................... 606/189

(58) Field of Classification Search .................. 606/189
See application file for complete search history.

(56) References Cited

U.S. PATENT DOCUMENTS 3,577,979 A * 5/1971 van der Gaast ............. 600/567
3,905,375 A * 9/1975 Toyama ...................... 606/189
4,139,011 A * 2/1979 Benoit et al. ................ 606/182
4,161,943 A * 7/1979 Nogier ........................ 600/12
4,375,815 A * 3/1983 Burns ......................... 606/182
5,540,710 A * 7/1996 Yoo ........................... 606/189
5,741,291 A * 4/1998 Yoo ........................... 606/189
2003/0040767 A1* 2/2003 Gavronsky ................. 606/189

* cited by examiner

*Primary Examiner*—Gary Jackson
*Assistant Examiner*—Julie A Szpira
(74) *Attorney, Agent, or Firm*—GWiPS

(57) ABSTRACT

A puncturing guidance tube for a long and fine needle is invented that is comprised of: a cylindrical body forming a long tubal-shape, a head portion forming a funnel shaped rim, an upper portion (31) of the cylindrical body having a large diameter, a lower portion (32) of the cylindrical body having a small diameter, a transition portion disposed between the upper portion and the lower portion, wherein the large diameter is gradually reduced to the small diameter of the cylindrical body, and a needle gateway (33) forming a lateral opening vertically all along the cylindrical body for easily removing the guidance tube from an operating needle, so that the long and fine needle can be punctured without buckling during an initial operation of the puncturing. The overall length of the tube is about two-third of the needle and the opening width of the needle gateway (33) is wide enough to pass out the needle.

3 Claims, 3 Drawing Sheets

[Fig. 1]
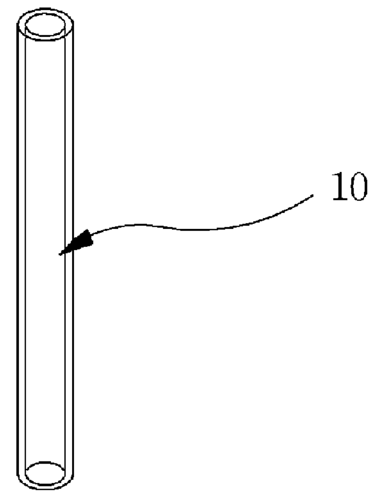
[Fig. 2]
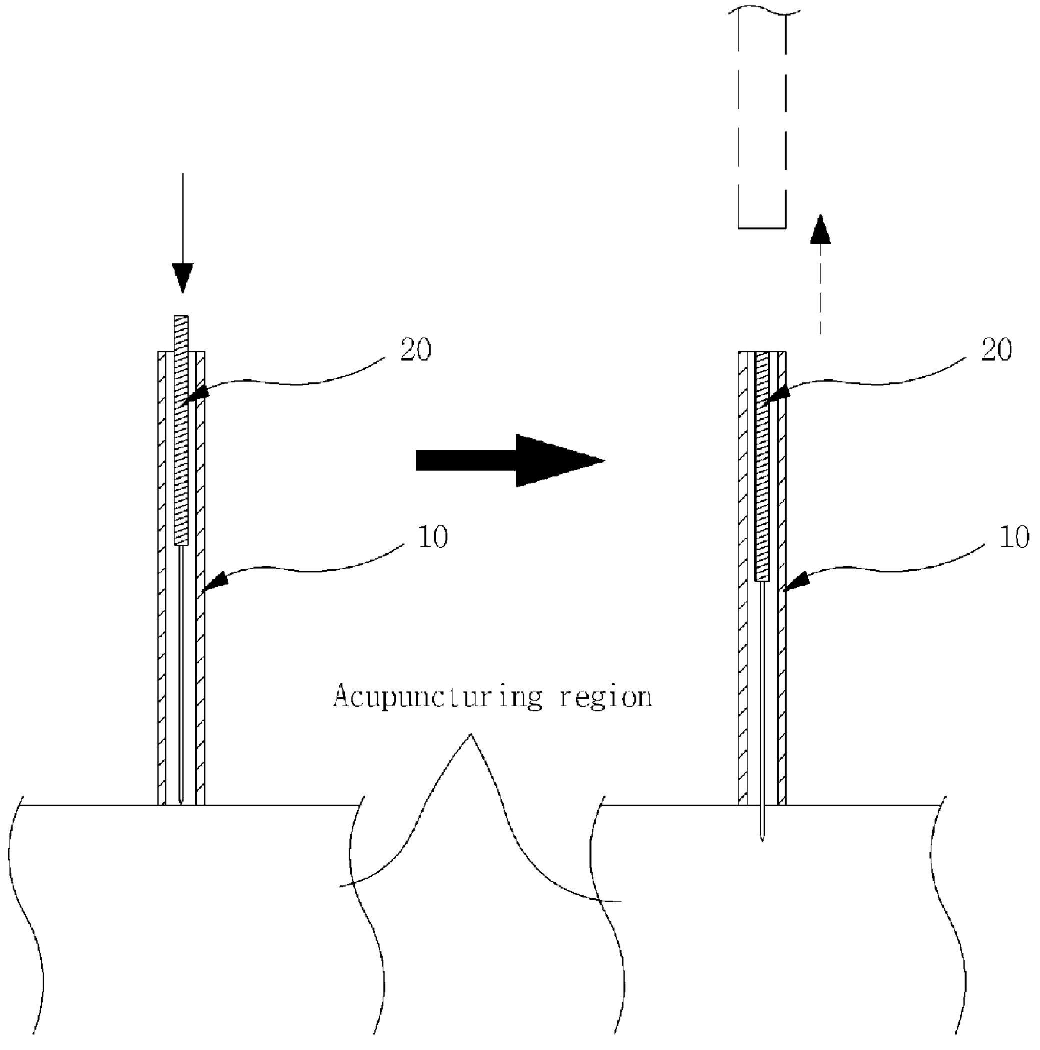

[Fig. 3]
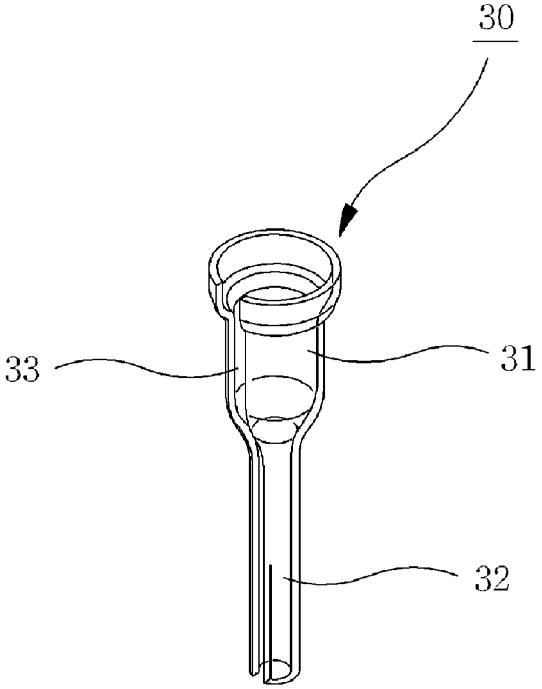
[Fig. 4]
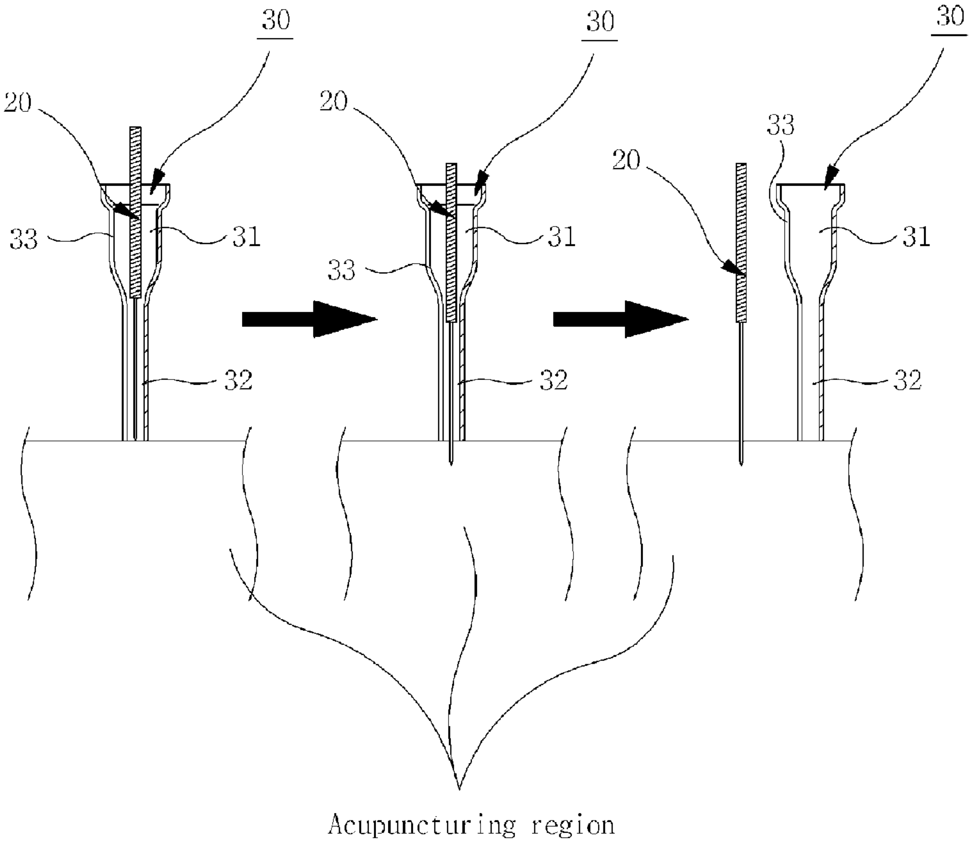

[Fig. 5]
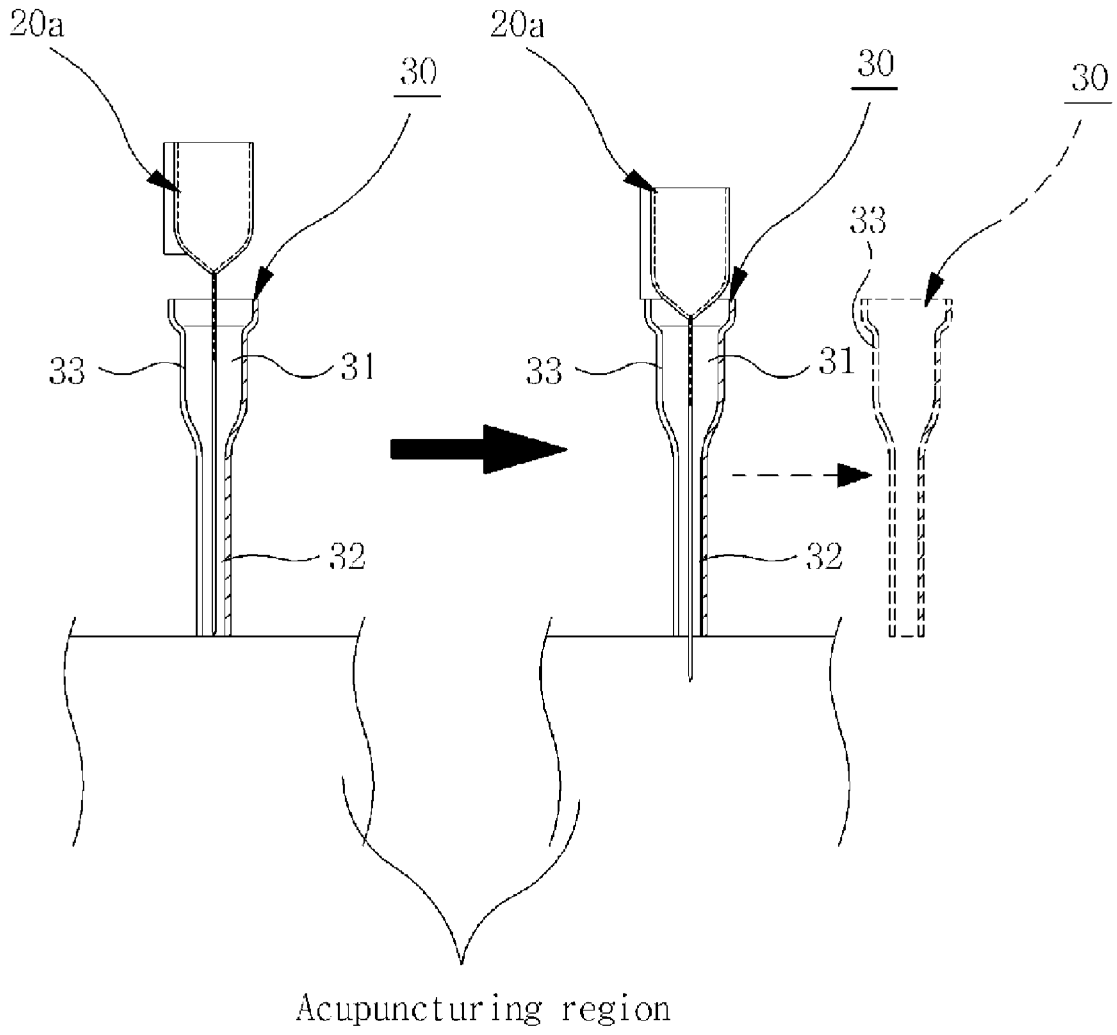

PUNCTURING GUIDANCE TUBE FOR A LONG AND FINE NEEDLE

BACKGROUND OF THE INVENTION

1. Field of the Invention

The present invention relates to an acupuncture needle tube, and more particularly, the tube consisted of a larger diameter upper tube, a smaller diameter lower tube and a needle gateway formed along with the lateral of the upper and lower tube used for acupuncturing by inserting acupuncture needle therein.

2. Description of the Related Prior Art

Generally, an acupuncture needle tube used in Chinese medicine is classified into one of 9 types, such as: a shear needle, a round-point needle, a DD needle, a sharp prismatic needle, a stiletto needle, a round-sharp needle, a filiform needle, a long needle, or a big needle.

Specifically, the filiform needle is the most commonly used type that is proper for adjusting a meridian system and treating arthritis caused by cold. Therefore, the filiform needle is widely used by lay people at home as well as by oriental medical doctors. The filiform needle includes a needle handle around which a gold or silver thread is wound and a needle stalk, which is connected to the needle handle and has a needle point.

Since the lay people using the filiform needle are not acupuncture experts, they usually use an acupuncture needle tube so as to reduce the acupuncture pain.

Referring to FIGS. 1 and 2, a conventional acupuncture needle tube 10 is cylindrical. After a filiform needle 20 is inserted into the acupuncture needle tube 10, the acupuncture needle tube 10 is placed on an acupuncturing region of a patient. When the user lightly flicks the needle handle using his/her index finger, a portion of the needle stalk is stuck in the acupuncturing region to a predetermined depth. Then, the user lifts the needle tube 10 in a direction as indicated by the broken arrow in FIG. 2, thereby completing the acupuncturing.

However, since the conventional needle tube 10 has a relatively small inner diameter of about 1.2-2 mm, it is difficult for a user whose sight is weak to insert the filiform needle 20 into the needle tube 10. Additionally, since the user inserts the filiform needle 20 with his/her bare fingers grasping the needle stalk, there is a hygienic problem.

That is, when the user grasps the needle stalk with his/her bare fingers, the filiform needle 20 is contaminated. Also, when the needle stalk 10 contacts the needle tube 10 as the user lifts the needle tube 10 after the needle stalk has been stuck in the acupuncture region, both the needle tube 10 and the filiform needle 20 are contaminated. The contamination of the filiform needle 20 may cause an infection of the acupuncture region.

Therefore, the conventional needle tube as it is designed, has a lot of problems in the possibility of infecting the blood vessel or reticular cavity of patients with weakened immunity, with advanced disease, or even those in good health.

SUMMARY OF THE INVENTION

Therefore, the present invention has been made in an effort to solve the above-described problems of the prior art.

It is an object of the present invention to provide an acupuncture needle tube that can prevent an acupuncture needle from being contaminated.

It is another object of the present invention to provide an acupuncture needle tube in which an acupuncture needle can be easily inserted.

To achieve the above objects, a puncturing guidance tube for a long and fine needle is provided comprising that: a cylindrical body forming a long tubal-shape, a head portion of the cylindrical body forming a funnel shaped rim, an upper portion of the cylindrical body having a large diameter, a lower portion of the cylindrical body having a small diameter, a transition portion of the cylindrical body disposed between the upper portion and the lower portion, wherein the large diameter is gradually reduced to the small diameter, and a needle gateway (33) of the cylindrical body forming a lateral opening vertically all along the cylindrical body for easily removing the guidance tube from an operating needle, so that the long and fine needle can be punctured without buckling during an initial operation of the puncturing.

The overall length of the guidance tube is about two-third of the needle, and an opening width of the needle gateway (33) is about 1.0 mm~2.0 mm.

The inner diameter of the upper portion is about 5.0 mm~8.0 mm and the inner diameter of the lower portion is about 1.5 mm~2.0 mm.

BRIEF DESCRIPTION OF THE DRAWINGS

FIG. 1 is a perspective view of a conventional needle tube.

FIG. 2 is a sectional view illustrating the use of a conventional needle tube depicted in FIG. 1.

FIG. 3 is a perspective view of an acupuncture needle tube according to an embodiment of the present invention.

FIG. 4 is a schematic view illustrating the use of an acupuncture needle tube depicted in FIG. 3.

FIG. 5 is a schematic view illustrating another use of an acupuncture needle tube depicted in FIG. 3.

DESCRIPTION OF THE PREFERRED EMBODIMENTS

The present invention will now be described more fully with reference to the accompanying drawings, in which exemplary embodiments of the invention are shown. Referring to FIG. 3, a needle tube 30 has a cylindrical body and includes a large diameter portion 31 formed on an upper portion of the cylindrical body. The large diameter portion 31 has an inner diameter of about 5-8 mm. The large diameter portion 31 is preferably formed in a trumpet shape.

The needle tube 30 further includes a small diameter portion 32 formed on the lower portion of the cylindrical body. The small diameter portion 32 extends from the lower end of the large diameter portion 31 to the lower end of the cylindrical body. The inner diameter of the small diameter portion 32 is about 1.5-2 mm.

The needle tube 30 has a needle gateway 33. The needle gateway 33 through which an acupuncture needle can go in to or out of the needle tube 30 is vertically formed along an outer circumference of the cylindrical body. The width of the needle gateway 33 is about 1-2 mm.

The use of the above-described needle tube 30 will be now described. Referring first to FIG. 4, since the inner diameter of the large diameter portion 31 of the needle tube 30 is large enough as compared with a diameter of the acupuncture needle 20, that even a user with weakened sight can easily insert the acupuncture needle into the needle tube 30 through the large diameter portion 31. Therefore, after the acupuncture needle tube 30 is placed on an acupuncturing region of a patient, the acupuncture needle 20 is inserted into the needle tube 30 through the large diameter portion 31 or the needle gateway 33. Then when the user lightly taps the needle handle using his/her index finger, a portion of the needle stalk is stuck in the acupuncturing region, to a predetermined depth.

Since the length of the acupuncture needle 20 varies (about 5-8 cm), it is preferable that the length of the needle tube 30 is about two-thirds to four-fifths of the length of the acupuncture needle 20. The length from the lower end of the large diameter portion 31 to the lower end of the small diameter portion 32 is preferably about 3-5 cm and the penetration depth of the acupuncture needle is preferably about 0.4-0.5 mm.

After the acupuncture needle is stuck in the acupuncturing region, the user may separate the needle tube 30 from the acupuncture needle 20 by lifting the needle tube 30. However, in the present invention, since the needle gateway 33 is formed on the needle tube 30, it is preferable that the needle tube 30 is separated from the acupuncture needle 20 through the needle gateway 33. When the user separates the needle tube 30 from the acupuncture needle 20 by lifting the needle tube 30, the needle tube 30 may contact the acupuncture needle 20. This may cause pain in the acupuncturing region. However, in the present invention, since the needle tube 30 is separated from the acupuncture needle 20 through the needle gateway 33, such contact problems can be solved.

FIG. 5 shows another example of a use of the needle tube 30 when an injection syringe 20*a*, instead of an acupuncture needle 20, is used.

The injection syringe 20*a* includes a syringe handle formed in a shape similar to the large diameter portion 31 of the needle tube 30. The injection syringe 20*a* further includes a hook step formed on an outer circumference of the syringe handle 20*a*. When the injection syringe 20*a* is inserted in the needle tube 30, the hook step is hooked on an upper end of the large diameter portion 31.

Referring to FIG. 5, after the acupuncture needle tube 30 is placed on an acupuncturing region of a patient, the injection syringe 20*a* is inserted into the needle tube 30 through the large diameter portion 31 or the needle gateway 33. Then, when the user lightly flicks or presses the syringe handle using his/her index finger, a portion of the stalk of the injection syringe 20*a* is stuck in the acupuncturing region, to a predetermined depth. At this point, the hook step formed on the outer circumference of the syringe handle 20*a* is hooked on the upper end of the large diameter portion 31 of the needle tube 30.

Then, as shown in FIG. 5, the user separates the needle tube 30 from the stuck injection syringe 20*a* through the needle gateway 33.

The puncturing guidance tube for a long and fine needle comprises that: a cylindrical body forming a long tubal-shape, a head portion of the cylindrical body forming a funnel shaped rim, an upper portion (31) of the cylindrical body having a large diameter, a lower portion (32) of the cylindrical body having a small diameter, a transition portion of the cylindrical body disposed between the upper portion and the lower portion, wherein the large diameter is gradually reduced to the small diameter of the cylindrical body, and a needle gateway (33) forming a lateral opening vertically all along the cylindrical body for easily removing the guidance tube from an operating needle, so that the long and fine needle can be punctured without buckling during an initial operation of the puncturing.

The overall length of the guidance tube is about two-third of the needle and the opening width of the needle gateway (33) is about 1.0 mm~2.0 mm.

The inner diameter of the upper portion is about 5.0 mm~8.0 mm and the inner diameter of the lower portion is about 1.5 mm~2.0 mm.

While the present invention has been particularly shown and described with reference to exemplary embodiments thereof, it will be understood by those of ordinary skill in the art that various changes in form and details may be made therein without departing from the spirit and scope of the present invention as defined by the following claims.

According to the present invention, the inventive needle tube has the large diameter portion with a diameter large enough relative to the diameter of the acupuncture needle, such that even a user with weakened sight can easily and hygienically insert the acupuncture needle into the needle tube through the large diameter portion with his/her fingers grasping the needle handle.

Also, since the acupuncture needle can be inserted into the needle tube through the needle gateway and can be separated from the needle tube through the needle gateway without lifting the needle tube, the invention solves the problem that the acupuncturing region may become infected by the contamination of the acupuncture needle and the needle tube caused when the user inserts the needle into the needle tube with his/her bare fingers grasping the needle stalk, or when the user lifts the needle tube to separate the needle tube from the needle.

What is claimed is:

1. A puncturing guidance tube for a long and fine needle in combination with the long and fine needle, comprising:

said long and fine needle (20), a cylindrical body having a long tubal-shape consisting of a head portion, an upper portion (31), a lower portion (32), a transition portion and a needle gateway (33), said head portion of the cylindrical body forming a funnel shaped rim, said upper portion (31) of the cylindrical body having a large diameter, said lower portion (32) of the cylindrical body having a small diameter, said transition portion of the cylindrical body disposed between the upper portion and the lower portion, wherein the large diameter is gradually reduced to the small diameter, and said needle gateway (33) of the cylindrical body formed a lateral opening vertically all along the cylindrical body for easily removing the puncturing guidance tube from an operating needle, so that the long and fine needle can be punctured without buckling during an initial operation of the puncturing.

2. The puncturing guidance tube according to claim 1, wherein an overall length of the cylindrical body is about two-third of the long and fine needle, and the needle gateway (33) has an opening width of about 1.0 mm~2.0 mm.

3. The puncturing guidance tube according to claim 1, wherein the inner diameter of the upper portion is about 5.0 mm~8.0 mm, and the inner diameter of the lower portion is about 1.5 mm~2.0 mm.

* * * * *